United States Patent
Noda et al.

(10) Patent No.: US 11,718,587 B2
(45) Date of Patent: *Aug. 8, 2023

(54) COMPOUND, EPOXY CURING CATALYST AND METHOD FOR PRODUCING COMPOUND

(71) Applicants: TOKYO OHKA KOGYO CO., LTD., Kawasaki (JP); Daicel Corporation, Osaka (JP)

(72) Inventors: Kunihiro Noda, Kawasaki (JP); Hiroki Chisaka, Kawasaki (JP); Issei Suzuki, Kawasaki (JP); Jiro Hikida, Kawasaki (JP); Dai Shiota, Kawasaki (JP); Kieko Hanano, Tokyo (JP); Kyohei Ishida, Tokyo (JP); Tsutomu Watanabe, Tokyo (JP); Kazuhiro Uehara, Tokyo (JP)

(73) Assignees: Tokyo Ohka Kogyo Co., Ltd., Kawasaki (JP); Daicel Corporation, Osaka (JP)

( * ) Notice: Subject to any disclaimer, the term of this patent is extended or adjusted under 35 U.S.C. 154(b) by 278 days.

This patent is subject to a terminal disclaimer.

(21) Appl. No.: 16/648,585

(22) PCT Filed: Sep. 26, 2018

(86) PCT No.: PCT/JP2018/035772
§ 371 (c)(1),
(2) Date: Mar. 18, 2020

(87) PCT Pub. No.: WO2019/065770
PCT Pub. Date: Apr. 4, 2019

(65) Prior Publication Data
US 2020/0283567 A1    Sep. 10, 2020

(30) Foreign Application Priority Data
Sep. 29, 2017   (JP) .................. 2017-191740

(51) Int. Cl.
*C07D 233/60* (2006.01)
*C07D 233/58* (2006.01)
(52) U.S. Cl.
CPC ......... *C07D 233/60* (2013.01); *C07D 233/58* (2013.01)
(58) Field of Classification Search
CPC .................... C07D 233/60; C07D 233/58
See application file for complete search history.

(56) References Cited

U.S. PATENT DOCUMENTS

| | | | | |
|---|---|---|---|---|
| 10,239,989 | B2* | 3/2019 | Noda | C08G 59/42 |
| 10,696,845 | B2* | 6/2020 | Noda | C08L 79/08 |
| 11,142,629 | B2* | 10/2021 | Hikida | H01L 51/5253 |
| 2015/0102332 | A1 | 4/2015 | Shin et al. | |
| 2017/0247334 | A1 | 8/2017 | Ishikawa et al. | |
| 2017/0327631 | A1* | 11/2017 | Noda | C08K 5/10 |
| 2019/0225804 | A1 | 7/2019 | Noda et al. | |
| 2019/0300674 | A1* | 10/2019 | Hikida | C07D 217/02 |

FOREIGN PATENT DOCUMENTS

| | | |
|---|---|---|
| CN | 106019862 A | 10/2016 |
| EP | 3002304 A1 | 4/2016 |
| JP | S 49-122599 A | 3/1973 |
| JP | 2011-116939 A | 6/2011 |
| JP | 2013-253233 A | 12/2013 |
| JP | 2014-098070 A | 5/2014 |
| JP | 2017-149914 A | 8/2014 |
| JP | 2015-079755 A | 4/2015 |
| JP | 2016-074890 A | 5/2016 |
| JP | 2016-194576 A | 11/2016 |
| TW | 201623248 A | 7/2016 |
| WO | WO 2011/025040 A1 | 3/2011 |
| WO | WO 2016/031928 A1 | 3/2016 |
| WO | WO-2016093254 A1 * | 6/2016 ......... C08G 59/4021 |

(Continued)

OTHER PUBLICATIONS

Gomaa et al., Synthesis and Biological Evaluation of 3-(1-H-Imidazol- and Triazol-1-yl)-2,2-dimethyl-3-[4-(naphthalen-2-ylamino)phenyl]propyl Derivatives as small Molecule Inhibitors of Retinoic Acid 4-Hydroxylase (CYP26). Journal of Medicinal Chemistry, 54(19), 6803-6811, Aug. 15, 2011.
Diez-Barra et al. "Double Michael addition of azoles to methyl propiolate:: a straightforward entry to ligands with two heterocyclic rings."Tetrahedron Letters, 45(37), 6937-6939, Sep. 6, 2004.
Extended European Search Report issued in European Patent Application No. 18861297.2, dated Jul. 20, 2020.
Mohamed S Gomaa et al. : "Novel retinoic acid 4-hydroxylase (CYP26) inhibitors based on a 3-(1-imidazol- and triazol-1-yl)-2,2-dimethyl-3-(4-(phenylamino)phenyl)propyl scaffold", Bioorganic & Medicinal Chemistry : A Tetrahedron Publication for the Rapid Dissemination of Full Original Research Papers and Critical Reviews on Biomolecular Chemistry, Medicinal Chemistry and Related Disciplines, Elsevier, NL, vol. 20, No. 14, May 30, 2012, pp. 4201-4207.
ACS.Registry Database, RN No. 1333206-22-6, Sep. 23, 2011.

* cited by examiner

Primary Examiner — Daniel R Carcanague
(74) Attorney, Agent, or Firm — Knobbe, Martens, Olson & Bear, LLP

(57) ABSTRACT

A novel compound suitable as an epoxy curing catalyst; an epoxy curing catalyst using the compound; and a method for producing the compound. A compound represented by formula (1) in which $X^{m+}$ represents an m valent counter cation, $R^1$ represents an aromatic group which may have a substituent; $R^2$ represents an alkylene group which may have a substituent; $R^3$ represents a halogen atom, a hydroxyl group, a mercapto group, a sulfide group, a silyl group, a silanol group, a nitro group, a nitroso group, a sulfonic acid ester group, a phosphino group, a phosphinyl group, a phosphonic acid ester group or an organic group; m represents an integer of 1 or more; n represents an integer of 0-3; and $R^2$ may bond with $R^1$ to form a cyclic structure.

4 Claims, No Drawings

(56) References Cited

FOREIGN PATENT DOCUMENTS

| WO | WO 2016/158679 A1 | 10/2016 | |
|----|---|---|---|
| WO | WO-2019065776 A1 * | 4/2019 | ............. C08G 59/40 |

COMPOUND, EPOXY CURING CATALYST AND METHOD FOR PRODUCING COMPOUND

This application is the U.S. National Phase under 35 U.S.C. § 371 of International Application PCT/JP2018/035772, filed Sep. 26, 2018, designating the U.S., and published in Japanese as WO 2019/065770 on Apr. 4, 2019 which claims priority to Japanese Patent Application No. 2017-191740, filed Sep. 29, 2017, the entire content of which is incorporated herein by reference.

PARTIES TO JOINT RESEARCH AGREEMENT

The present invention was made pursuant to a joint research agreement between Tokyo Ohka Kogyo Co., Ltd. and Daicel Corporation.

TECHNICAL FIELD

The present invention relates to a novel compound suitable as an epoxy curing catalyst, an epoxy curing catalyst using the compound, and a method for producing the compound.

BACKGROUND ART

A curable composition including an epoxy compound, a curing agent, and a curing catalyst has widely been used in various applications such as adhesive applications, sealing applications of various electronic components, and matrix formation applications of fiber-reinforced composite materials. In such a curable composition, curability by a curing agent and a curing catalyst is required to be further improved (for example, Patent Document 1).

On the other hand, Patent Document 2 describes an imidazole compound having a specific structure giving a metal surface treatment liquid having an excellent effect of suppressing migration or oxidation of wiring surface.

Patent Document 1: Japanese Unexamined Patent Application, Publication No. 2016-074890
Patent Document 2: PCT International Publication No. WO2016/031928

DISCLOSURE OF THE INVENTION

Problems to be Solved by the Invention

In view of the requirement of further improvement of curability of a curable composition including an epoxy compound of the above-mentioned conventional technology, the present invention has an object to provide a novel compound suitable as an epoxy curing catalyst, an epoxy curing catalyst using the compound, and a method for producing the compound.

Means for Solving the Problems

The present inventors have found that a novel compound including a plurality of residues exhibiting epoxy curability inside a molecule in the same or different conditions can improve the curability of a curable composition including an epoxy compound (for example, improve heat resistance of an epoxy cured product) and is suitable as an epoxy curing catalyst, and that when the compound includes a plurality of different residues exhibiting epoxy curability in different conditions, it can exhibit gradual epoxy curability during heating, and have completed the present invention.

A first aspect of the present invention is a compound represented by the following formula (1).

[Chem. 1]

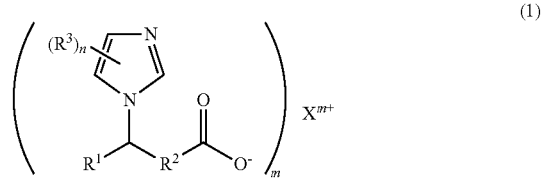

(In the formula (1), $X^{m+}$ represents an m-valent counter cation; $R^1$ represents an optionally substituted aromatic group; $R^2$ represents an optionally substituted alkylene group; $R^3$ represents a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; m is an integer of 1 or more; n is an integer of 0 or more and 3 or less; and $R^2$ may be bonded to $R^1$ to form a cyclic structure.)

A second aspect of the present invention is an epoxy curing catalyst including the compound of the first aspect. A third aspect of the present invention is a method for producing the compound of the first aspect, the method including producing the compound of the first aspect by neutralizing the compound represented by the formula (10) below, and a base capable of forming an m-valent counter cation $X^{m+}$ in the presence or absence of a solvent.

[Chem. 2]

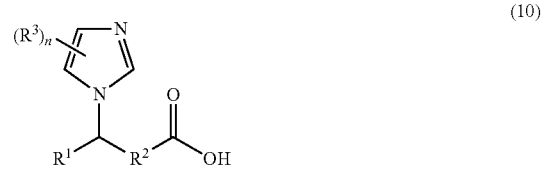

(In the formula (10), $R^1$ is an optionally substituted aromatic group; $R^2$ is an optionally substituted alkylene group; $R^3$ is a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; n is an integer of 0 or more and 3 or less; and $R^2$ may be bonded to $R^1$ to form a cyclic structure.)

Effects of the Invention

The compound of the present invention is excellent in epoxy curability (for example, heat resistance of an epoxy cured product), and is suitable as an epoxy curing catalyst. Furthermore, the present invention can provide an epoxy curing catalyst using the compound, and a method for producing the compound.

PREFERRED MODE FOR CARRYING OUT THE INVENTION

Hereinafter, embodiments of the present invention will now be described in detail, but the present invention is not necessarily limited to the following embodiments and can be implemented with appropriate modifications within the purpose of the present invention. Furthermore, in this specification, " . . . to . . . " represents " . . . or more and . . . or less" unless otherwise notified.

<<Compound>>

The compound of the first aspect is represented by the following formula (1).

[Chem. 3]

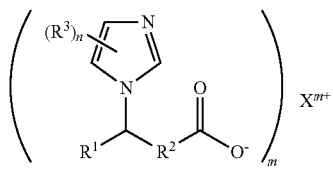

(1)

(In the formula (1), $X^{m+}$ represents an m-valent counter cation; $R^1$ represents an optionally substituted aromatic group; $R^2$ represents an optionally substituted alkylene group; $R^3$ represents a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; m is an integer of 1 or more; n is an integer of 0 or more and 3 or less; and $R^2$ may be bonded to $R^1$ to form a cyclic structure.)

The m-valent counter cation $X^{m+}$ is preferably an acyclic or cyclic nitrogen-containing aliphatic cation, a nitrogen-containing aromatic cation, or a metal cation. m is an integer of preferably 1 or more and 3 or less, more preferably 1 or 2, and further preferably 1. Preferably, the above-listed acyclic or cyclic nitrogen-containing aliphatic cation is represented by any one of the following formulae (2) to (4) below.

[Chem. 4.]

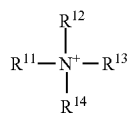

(2)

(In the formula (2), $R^{11}$ to $R^{14}$ each independently represent a hydrogen atom, an optionally substituted alkyl group, an optionally substituted cycloalkyl group, an optionally substituted alkenyl group, an optionally substituted alkynyl group, an optionally substituted aryl group, an optionally substituted aralkyl group, or an optionally substituted heterocyclic group, and at least two selected from $R^{11}$ to $R^{14}$ may link together to form a ring.)

In the formula (2), as the optionally substituted alkyl group, an alkyl group having 1 or more and 30 or less carbon atoms is preferable. Specific examples of the optionally substituted alkyl group include a methyl group, an ethyl group, an n-propyl group, an n-butyl group, an n-hexyl group, an n-octyl group, an n-decyl group, an n-dodecyl group, an n-octadecyl group, an isopropyl group, an isobutyl group, a sec-butyl group, a tert-butyl group, 1-ethylpentyl group, a trifluoromethyl group, a 2-ethyl hexyl group, a phenacyl group, a 1-naphthoylmethyl group, a 2-naphthoylmethyl group, a 4-methylsulfanyl phenacyl group, a 4-phenyl sulfanylphenacyl group, a 4-dimethylamino phenacyl group, a 4-cyanophenacyl group, a 4-methylphenacyl group, a 2-methylphenacyl group, a 3-fluorophenacyl group, a 3-trifluoromethylphenacyl group, a 3-nitrophenacyl group, and the like. As the optionally substituted cycloalkyl group, a cycloalkyl group having 5 or more and 30 or less carbon atoms is preferable. Specific examples of the optionally substituted cycloalkyl group include a cyclopentyl group, a cyclohexyl group, and the like.

As the optionally substituted alkenyl group, an alkenyl group having 2 or more and 10 or less carbon atoms is preferable. Specific examples of the optionally substituted alkenyl group include a vinyl group, an aryl group, a styryl group, and the like. As the optionally substituted alkynyl group, an alkynyl group having 2 or more and 10 or less carbon atoms is preferable. Specific examples of the optionally substituted alkynyl group include an ethynyl group, a propynyl group, a propargyl group, and the like. As the optionally substituted aryl group, an aryl group having 6 or more and 30 or less carbon atoms is preferable. Specific examples of the optionally substituted aryl group include a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quaterphenyl group, an o-tolyl group, an m-tolyl group, a p-tolyl group, a xylyl group, an o-cumenyl group, an m-cumenyl group, a p-cumenyl group, a mesityl group, a pentalenyl group, a binaphthalenyl group, a ternaphthalenyl group, a quaternaphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quateranthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, and the like.

As the optionally substituted aralkyl, an aralkyl group having 7 or more and 20 or less carbon atoms is preferable, and examples thereof include a benzyl group, a phenethyl group, an α-naphthyl methyl group, a β-naphthyl methyl group, a 2-α-naphthyl ethyl group, a 2-β-naphthyl ethyl group, and the like. As the optionally substituted heterocyclic group, an aromatic or aliphatic heterocycle including a nitrogen atom, an oxygen atom, a sulfur atom, and a phosphorus atom is preferable. Specific examples of the heterocycle include a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiinyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naphthyridinyl group, a quinoxalinyl group, a quinazolinyl group, a cinnolinyl group, a pteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxazinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinuclidinyl group, a morpholinyl group, and a thioxanthryl group.

A hydrogen atom of the optionally substituted alkyl group, the optionally substituted cycloalkyl group, the optionally substituted alkenyl group, the optionally substituted alkynyl group, the optionally substituted aryl group, the optionally substituted aralkyl group, or the optionally substituted heterocyclic group mentioned above may be substituted with further the other substituent.

Examples of such a substituent may include a halogen atom (for example, a fluorine atom, a chlorine atom, a bromine atom, and an iodine atom); a cyano group; a nitro group; an alkoxy group (a methoxy group, an ethoxy group, a tert-butoxy group, and the like); an aryloxy group (a phenoxy group, a p-tolyloxy group, and the like); an organoxycarbonyl group (a methoxycarbonyl group, a butoxycarbonyl group, a phenoxylcarbonyl group, a vinyloxycarbonyl group, and aryloxycarbonyl, group, and the like); an acyloxy group (an acetoxy group, a propionyloxy group, a benzoyl oxy group, and the like); an acyl group (an acetyl group, a benzoyl group, an isobutyryl group, an acryloyl group, a methacryloyl group, a methoxalyl group, and the like); an alkylsulfanyl group (a methylsulfanyl group, a tert-butylsulfanyl group, and the like); an arylsulfanyl group (a phenylsulfanyl group, a p-tolylsulfanyl group, and the like); an alkyl amino group (a methyl amino group, a cyclohexyl amino group, and the like); a diakyl amino group (a dimethyl amino group, a diethyl amino group, a morpholino group, a piperidino group, and the like); an aryl amino group (a phenyl amino group, a p-tolyl amino group, and the like); an alkyl group (a methyl group, an ethyl group, a tert-butyl group, a dodecyl group, and the like); an aryl group (a phenyl group, a p-tolyl group, a xylyl group, a cumenyl group, a naphthyl group, an anthryl group, a phenanthryl group, and the like); a hydroxy group; a carboxy group; a sulfonamide group; a formyl group; a mercapto group; a sulfo group; a mesyl group; a p-toluenesulfonyl group; an amino group; a nitroso group; a trifluoromethyl group, a trichloromethyl group; a trimethylsilyl group; a phosphinico group; a phosphono group; an alkyl sulfonyl group; an aryl sulfonyl group; a trialkyl ammonium group; a dimethylsulfoniumyl group; a triphenylphenancylphosphoniumyl group, and the like.

In the formula (2), when at least two selected from $R^{11}$ to $R^{14}$ are bonded to each other to form a ring, examples of the linking group include an alkylene group, a cycloalkylene group or a divalent group obtained by bonding thereof. The number of carbon atoms of the linking group is preferably 1 or more and 10 or less. The ring formed of at least two selected from $R^{11}$ to $R^{14}$ may include a ring-forming atoms and an oxygen atom.

$$(R^{21})_2N^+=C(NR^{22}_2)_2 \quad (3)$$

(In the formula (3), $R^{21}$ each independently represents a hydrogen atom, an alkyl group or a cycloalkyl group, $R^{22}$ each independently represents a hydrogen atom, an alkyl group, a cycloalkyl group, a —C(=$NR^{23}$)—$NR^{23}_2$ (three $NR^{23}$ each independently represents a hydrogen atom, an alkyl group, or a cycloalkyl group), or =C(—$NR^{24}_2)_2$ (four $R^{24}$ each independently represents a hydrogen atom or an organic group).)

As the alkyl group in $R^{21}$ to $R^{23}$, an alkyl group having 1 or more and 10 or less carbon atoms is preferable. Specific examples of the alkyl group include a methyl group, an ethyl group, a propyl group, a butyl group, a hexyl group, an octyl group, a decyl group, a dodecyl group, an octadecyl group, an isopropyl group, an isobutyl group, a sec-butyl group, a tert-butyl group, a 1-ethylpentyl group, and the like. As the cycloalkyl group in $R^{21}$ to $R^{23}$, a cycloalkyl group having 5 or more and 30 or less carbon atoms is preferable. Specific examples of the cycloalkyl group include a cyclopentyl group, a cyclohexyl group, and the like. Examples of the organic group for $R^{24}$ include an alkyl group, a cycloalkyl group, an aralkyl group, an aryl group, and the like. Examples of cations represented by the formula (3) include 1,2-diisopropyl-3-[bis(dimethylamino)methylene]guanidinium cation, 1-methylbiguanidium cation, 1-n-butylbiguanidium cation, 1-(2-ethyl hexyl)biguanidium cation, 1-n-octadecylbiguanidium cation, 1,1-dimethylbiguanidium cation, 1,1-diethylbiguanidium cation, 1-cyclo hexyl biguanidium cation, 2-ethyl-1,1,3,3-tetramethylguanidinium cation, 1-benzylguanidinium cation, 1,3-dibenzylguanidinium cation, 1-benzyl-2,3-dimethylguanidinium cation, 1-phenylguanidinium cation, and the like. Among these cations, 1,2-diisopropyl-3-[bis(dimethylamino)methylene]guanidinium is preferable.

[Chem. 5]

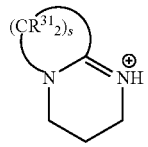

(4)

(In the formula (4), $R^{31}$ each independently represents a hydrogen atom or an organic group, and s represents an integer of 2 or more and 6 or less.)

Examples of the organic group for $R^{31}$ include an alkyl group, a cycloalkyl group, an aralkyl group, an aryl group, and the like. The alkyl group above, the cycloalkyl group above, the aralkyl group above, and the aryl group above may have a substituent, respectively. Examples of the substituent may include a halogen atom (for example, a fluorine atom, a chlorine atom, a bromine atom, and an iodine atom); a cyano group; a nitro group; an alkoxy group (a methoxy group, an ethoxy group, a tert-butoxy group, and the like); an aryloxy group (a phenoxy group, a p-tolyloxy group, and the like); an organoxycarbonyl group (a methoxycarbonyl group, a butoxycarbonyl group, a phenoxylcarbonyl group, a vinyloxycarbonyl group, and aryloxycarbonyl, group, and the like); an acyloxy group (an acetoxy group, a propionyloxy group, a benzoyl oxy group, and the like); an acyl group (an acetyl group, a benzoyl group, an isobutyryl group, an acryloyl group, a methacryloyl group, a methoxalyl group, and the like); an alkylsulfanyl group (a methylsulfanyl group, a tert-butylsulfanyl group, and the like); an arylsulfanyl group (a phenylsulfanyl group, a p-tolylsulfanyl group, and the like); an alkyl amino group (a methyl amino group, a cyclohexyl amino group, and the like); a diakyl amino group (a dimethyl amino group, a diethyl amino group, a morpholino group, a piperidino group, and the like); an aryl amino group (a phenyl amino group, a p-tolyl amino group, and the like); an alkyl group (a methyl group, an ethyl group, a tert-butyl group, a dodecyl group, and the like); an aryl group (a phenyl group, a p-tolyl group, a xylyl group, a cumenyl group, a naphthyl group, an anthryl group, a phenanthryl group, and the like); a hydroxy group; a carboxy group; a sulfonamide group; a formyl group; a mercapto group; a sulfo group; a mesyl group; a p-toluenesulfonyl group; an amino group; a nitroso group; a trifluoromethyl group, a trichloromethyl group; a trimethylsilyl group; a phosphinico group; a phosphono group; an alkyl sulfonyl group; an aryl sulfonyl group; a trialkyl ammonium group; a dimethylsulfoniumyl group; a triphenylphenancylphosphoniumyl group, and the like. s is an integer of preferably 3 or more and 5 or less, and more preferably 3 or 4.

As the nitrogen-containing aromatic cation of the counter cation $X^{m+}$, the cation represented by any one of the following formulae (5) to (13) below is preferable.

[Chem. 6]

(5)

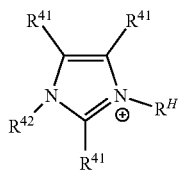

(6)

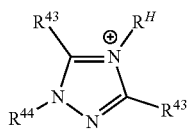

(7)

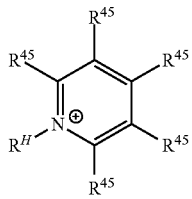

(8)

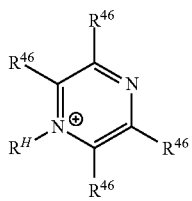

(9)

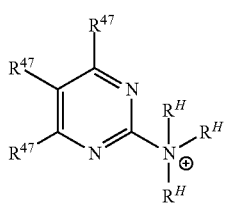

(10)

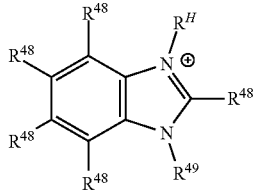

(11)

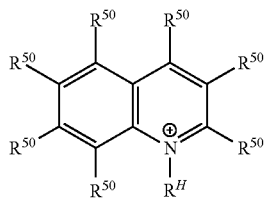

(12)

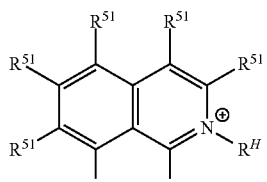

(13)

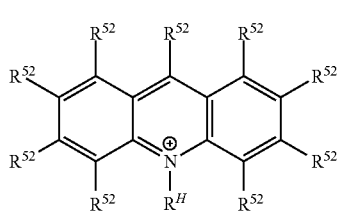

(In the formula, $R^H$ each independently represents a hydrogen atom or an alkyl group; $R^{41}$, $R^{43}$, $R^{45}$, $R^{46}$, $R^{47}$, $R^{48}$, $R^{50}$, $R^{51}$, and $R^{52}$ each independently represents a hydrogen atom, a halogen atom, a cyano group, a nitro group, an alkyl group, a cycloalkyl group, an alkenyl group, or an alkynyl group; $R^{42}$, $R^{44}$, and $R^{49}$ each independently represents a hydrogen atom, a halogen atom, an alkyl group, a cycloalkyl group, an alkenyl group, or an alkynyl group. $R^{41}$ to $R^{52}$ each independently may be substituted with a halogen atom, a cyan group, or a nitro group; $R^{41}$ and $R^{42}$ may be bonded to each other to form a ring; at least two $R^{41}$s may be bonded to each other to form a ring; $R^{43}$ and $R^{44}$ may be bonded to each other to form a ring; two $R^{43}$s may be bonded to each other to form a ring; at least two $R^{45}$s may be bonded to each other to form a ring; at least two $R^{46}$s may be bonded to each other to form a ring; at least two $R^{47}$s may be bonded to each other to form a ring; $R^{48}$ and $R^{49}$ may be bonded to each other to form a ring; at least two $R^{48}$s may be bonded to each other to form a ring; at least two $R^{50}$s may be bonded to each other to form a ring; at least two $R^{51}$s may be bonded to each other to form a ring; at least two $R^{52}$s may be bonded to each other to form a ring.)

Examples of the halogen atom as $R^{41}$ to $R^{52}$ include a fluorine atom, a chlorine atom, a bromine atom, or an iodine atom. The alkyl group for $R^H$, and $R^{41}$ to $R^{52}$ may be a linear alkyl group or a branched alkyl group. The number of carbon atoms of the alkyl group is not particularly limited, but the number of carbon atoms of the alkyl group is preferably 1 or more and 20 or less, more preferably 1 or more and 10 or less, and further preferably 1 or more and 5 or less. Specific examples of the alkyl group for $R^H$, and $R^{41}$ to $R^{52}$ include a methyl group, an ethyl group, an n-propyl group, an isopropyl group, an n-butyl group, an isobutyl group, an sec-butyl group, a tert-butyl group, an n-pentyl group, an isopentyl group, a tert-pentyl group, an n-hexyl group, an n-heptyl group, an n-octyl group, a 2-ethyl-n-hexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group.

The cycloalkyl group for $R^{41}$ to $R^{52}$ is preferably a cycloalkyl group having 5 or more and 30 or less carbon atoms. Specific examples of the cycloalkyl group include a cyclopentyl group, a cyclohexyl group, and the like. The alkenyl group for $R^{41}$ to $R^{52}$ is preferably an alkenyl group having 2 or more and 10 or less carbon atoms. Specific examples of the alkenyl group include a vinyl group, an aryl group, a styryl group, and the like. The alkynyl group for $R^{41}$ to $R^{52}$ is preferably an alkynyl group having 2 or more and 10 or less carbon atoms. Specific examples of the alkynyl group include an ethynyl group, a propynyl group, a propargyl group, and the like.

When m is an integer of 2 or more, the acyclic or cyclic nitrogen-containing aliphatic cation of the m-valent counter cation $X^{m+}$ is preferably a cation represented by any one of the following formulae (14) to (16) below.

[Chem. 7]

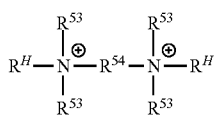
(14)

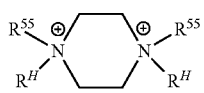
(15)

(16)

(In the above formula, $R^H$ each independently represents a hydrogen atom or an alkyl group; $R^{53}$ and $R^{55}$ each independently an alkyl group or a cycloalkyl group; $R^{54}$ represents an alkylene group, a cycloalkylene group or a divalent group obtained by bonding thereof; $R^{56}$ represents an alkylene group; $R^{53}$ to $R^{56}$ each independently may be substituted with a halogen atom, a cyano group or a nitro group; at least two $R^{53}$s may be bonded to each other to form a ring; $R^{53}$ and $R^{54}$ may be bonded to each other to form a ring; two $R^{55}$s may be bonded to each other to form a ring.)

Specific examples and preferable examples of $R^H$ include the same specific examples and preferable examples mentioned above. Examples of the alkyl group for $R^H$ and $R^{53}$ to $R^{55}$ include the same alkyl groups as those of the specific examples and preferable examples mentioned above as the alkyl group for $R^H$ and $R^{41}$ to $R^{52}$. The cycloalkyl group for $R^{53}$ to $R^{55}$ includes the same cycloalkyl groups as those of the specific examples and preferable examples mentioned above as the cycloalkyl group for $R^{41}$ to $R^{52}$. The alkylene group for $R^{56}$ includes an alkylene group having 1 or more and 5 or less carbon atoms. Examples of the alkylene group include a methylene group, an ethylene group, a propylene group, a butylene group, and the like.

When m is an integer of 2 or more, examples of the nitrogen-containing aromatic cation as the m-valent counter cation $X^{m+}$ include cations of divalent or more having a 2,2-bipyridinium skeleton, a 3,3-bipyridinium skeleton, a 4,4-bipyridinium skeleton, a 2,2-bipyrazinium skeleton, a 4,4-biquinolinium skeleton, a 4,4-biisoquinolinium skeleton, a 4-[2-(4-pyridinium)vinyl]pyridinium skeleton, or a 4-[4-(4-pyridinium)phenyl]pyridinium skeleton in the molecule.

The metal cation as the counter cation $X^{m+}$ is preferably cations of metal atoms selected from the group consisting of a typical metal element, a transition metal element, and a semimetal element, or cations of an atomic group including the above-mentioned metal atoms. Examples of the above typical metal element include alkali metal elements (metal elements including elements belonging to Group 1 excluding hydrogen, for example, sodium and potassium), alkali earth metal element (metal elements including elements belonging to Group 2, for example, magnesium), metal elements including elements belonging to Group 12 (for example, zinc), metal elements including elements belonging to Group 13 excluding boron (for example, aluminum), metal elements including elements belonging to Group 14 excluding carbon and silicon (for example, tin), metal elements including elements belonging to Group 15 excluding nitrogen, phosphorus, and arsenic (for example, antimony), and metal elements including elements belonging to Group 16 excluding oxygen, sulfur, selenium, and tellurium (for example, polonium). Examples of the above transition metal element include elements including elements belonging to Groups 3 to 11 (for example, hafnium). Examples of the above semimetal element include elements such as boron, silicon, arsenic, selenium, and tellurium. Examples of cations of the atomic group including the above metal atoms include the atomic group including both a metal atom and a nonmetal atom, and the like. Specific examples thereof include $[ZrO]^{2+}$, $[(C_2H_5O)Al]^{2+}$, $[(n-C_4H_9)_2Sn-O-Sn(n-C_4H_9)_2]^{2+}$, and the like.

In the formula (1), $R^1$ represents an optionally substituted aromatic group. The optionally substituted aromatic group may be either an optionally substituted aromatic hydrocarbon group or an optionally substituted aromatic heterocyclic group.

The type of the aromatic hydrocarbon group is not particularly limited as long as it does not interfere with the object of the present invention. The aromatic hydrocarbon group may be a monocyclic aromatic group, may be formed by condensation of two or more aromatic hydrocarbon groups, or may be formed by bonding of two or more aromatic hydrocarbon groups through a single bond. The aromatic hydrocarbon group is preferably a phenyl group, a naphthyl group, a biphenylyl group, an anthryl group, and a phenanthrenyl group.

The type of the aromatic heterocyclic group is not particularly limited as long as it does not interfere with the object of the present invention. The aromatic heterocyclic group may be either a monocyclic group or a polycyclic group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzimidazolyl group.

Examples of the substituent, which a phenyl group, a polycyclic aromatic hydrocarbon group, or an aromatic heterocyclic group may have, include a halogen atom, a hydroxyl group, a mercapto group, a sulfide group, a silyl group, a silanol group, a nitro group, a nitroso group, a sulfino group, a sulfo group, a sulfonate group, a phosphino group, a phosphinyl group, a phosphono group, a phosphonate group, an amino group, an ammonio group, and an organic group. When the phenyl group, the polycyclic aromatic hydrocarbon group, or the aromatic heterocyclic group have plural substituents, the plural substituents may be the same or different.

When the substituent, which the aromatic group has, is an organic group, examples of the organic group include an alkyl group, an alkenyl group, a cycloalkyl group, a cycloalkenyl group, an aryl group, an aralkyl group, or the like. This organic group may have a bond or a substituent, other than a hydrocarbon group such as a heteroatom, in the organic group. This organic group may be either linear, branched, or cyclic. This organic group is usually monovalent, but can be a divalent or higher polyvalent organic group when forming a cyclic structure.

When the aromatic group has a substituent on neighboring carbon atoms, two substituents bonded on neighboring carbon atoms may be bonded to form a cyclic structure. Examples of the cyclic structure include an aliphatic hydrocarbon ring, and an aliphatic ring having a heteroatom.

When the substituent, which the aromatic group has, is an organic group, the bond included in the organic group is not particularly limited, as long as it does not impair the effect of the present invention; and the organic group may include a bond having a heteroatom such as an oxygen atom, a nitrogen atom, or a silicon atom. Specific examples of the bonded containing a heteroatom include, an ether bond, a thioether bond, a carbonyl bond, a thiocarbonyl bond, an ester bond, an amide bond, an amino bond ($-NR^A-$: $R^A$ represents a hydrogen atom or a monovalent organic group), a urethane bond, an imino bond ($-N=C(-R^B)-$, $-C(=NR^B)-$: $R^B$ represents a hydrogen atom or a monovalent organic group), a carbonate bond, a sulfonyl bond, a sulfinyl bond, an azo bond, and the like.

From the viewpoint of heat resistance of the imidazole compound represented by the formula (1), the bond containing a heteroatom, which an organic group may have, is preferably an ether bond, a thioether bond, a carbonyl bond, a thiocarbonyl bond, an ester bond, an amide bond, an amino bond ($-NR^A-$: $R^A$ R represents a hydrogen atom or a monovalent organic group), an urethane bond, an imino bond ($-N=C(-R^B)-$, $-C(=NR^B)-$: $R^B$ represents a hydrogen atom or a monovalent organic group), a carbonate bond, a sulfonyl bond, and a sulfinyl bond.

When the organic group is a substituent other than the hydrocarbon group, the type of substituents other than the hydrocarbon group is not particularly limited as long as it does not interfere with the object of the present invention. Specific examples of the substituent other than the hydrocarbon group include a halogen atom, a hydroxyl group, a mercapto group, a sulfide group, a cyano group, an isocyano group, a cyanate group, an isocyanate group, a thiocyanate group, an isothiocyanate group, an silyl group, an silanol group, an alkoxy group, an alkoxycarbonyl group, an amino group, a monoalkylamino group, a dialkylamino group, a monoarylamino group, a diarylamino group, a carbamoyl group, a thiocarbamoyl group, a nitro group, a nitroso group, a carboxylate group, an acyl group, an acyloxy group, a sulfino group, a sulfonate group, a phosphino group, a phosphinyl group, a phosphonate group, an alkyl ether group, an alkenyl ether group, an alkyl thioether group, an alkenyl thioether group, an aryl ether group, an aryl thioether group, and the like. The hydrogen atom included in the substituent mentioned above may be substituted with a hydrocarbon group. The hydrocarbon group included in the substituent mentioned above may be either linear, branched, or cyclic.

The substituent, which a phenyl group, a polycyclic aromatic hydrocarbon group, or an aromatic heterocyclic group has, is preferably an alkyl group having 1 or more and 12 or less carbon atoms, an aryl group having 1 or more and 12 or less carbon atoms, an alkoxy group having 1 or more and 12 or less carbon atoms, an aryloxy group having 1 or more and 12 or less carbon atoms, an arylamino group having 1 or more and 12 or less carbon atoms, and a halogen atom.

As $R^1$, a phenyl group, a furyl group, and a thienyl group, each of which is optionally substituted, are preferable because a compound represented by formula (1) can be synthesized inexpensively and easily and the solubility of the compound in water or an organic solvent is good.

In the formula (1), $R^2$ is an optionally substituted alkylene group. The substituent, which an alkylene group may have, is not particularly limited, as long as it does not interfere with the object of the present invention. Specific examples of the substituent, which an alkylene group may have, include a hydroxyl group, an alkoxy group, an amino group, a cyano group, a halogen atom, and the like. The alkylene group may be either a linear alkylene group or a branched alkylene group, and is preferably a linear alkylene group. The number of carbon atoms of the alkylene group is not particularly limited, but is preferably 1 or more and 20 or less, preferably 1 or more and 10 or less, and more preferably 1 or more and 5 or less. Note here that the number of carbon atoms of an alkylene group does not include the number of substituent carbon atoms bonded to the alkylene group.

The alkoxy group as the substituent bonded to the alkylene group may be either a linear alkoxy group or a branched alkoxy group. The number of carbon atoms of the alkoxy group as the substituent is not particularly limited, but is preferably 1 or more and 10 or less, more preferably 1 or more and 6 or less, and particularly preferably 1 or more and 3 or less.

The amino group as the substituent bonded to the alkylene group may be a monoalkylamino group or a dialkylamino group. The alkyl group included in the monoalkylamino group or dialkylamino group may be either a linear alkyl group or a branched alkyl group. The number of carbon atoms of the alkyl group included in the monoalkylamino group or dialkylamino group is not particularly limited, but is preferably 1 or more and 10 or less, more preferably 1 or more and 6 or less, and particularly preferably 1 or more and 3 or less.

Specific examples of the alkylene group suitable as $R^2$ include a methylene group, an ethane-1,2-diyl group, an n-propane-1,3-diyl group, an n-propane-2,2-diyl group, an n-butane-1,4-diyl group, an n-pentane-1,5-diyl group, an n-hexane-1,6-diyl group, an n-heptane-1,7-diyl group, an n-octane-1,8-diyl group, an n-nonane-1,9-diyl group, an n-decane-1,10-diyl group, an n-undecane-1,11-diyl group, an n-dodecane-1,12-diyl group, an n-tridecane-1,13-diyl group, an n-tetradecane-1,14-diyl group, an n-pentadecane-1,15-diyl group, an n-hexadecane-1,16-diyl group, an n-heptadecane-1,17-diyl group, an n-octadecane-1,18-diyl group, an n-nonadecane-1,19-diyl group, and an n-icosane-1,20-diyl group.

$R^3$ represents a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; and n is an integer of 0 or more and 3 or less. When n is an integer of 2 to 3, a plurality of $R^3$ may be the same or different.

When $R^3$ is an organic group, the organic group is the same as an organic group, which an aromatic group may have as a substituent, as for $R^1$.

When $R^3$ is an organic group, the organic group is preferably an alkyl group, an aromatic hydrocarbon group, and an aromatic heterocyclic group. The alkyl group is preferably a linear or branched alkyl group having 1 or more and 8 or less carbon atoms, and more preferably a methyl group, an ethyl group, an n-propyl group, and an isopropyl group. The aromatic hydrocarbon group is preferably a phenyl group, a naphthyl group, a biphenylyl group, an anthryl group, and a phenanthrenyl group, more preferably a phenyl group and a naphthyl group, and particularly preferably a phenyl group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzimidazolyl group, and more preferably a furyl group and a thienyl group.

When $R^3$ is an alkyl group, the position of the alkyl group bonding on an imidazole ring is preferably any one of 2-, 4-, and 5-positions, and more preferably 2-position. When $R^3$ is an aromatic hydrocarbon group and an aromatic heterocyclic group, the position of these groups bonding on imidazole is preferably 2-position.

Among the compounds represented by the above-mentioned formula (1), from the viewpoint that a compound can be synthesized inexpensively and easily and the solubility of the compound in water or an organic solvent is good, the compound is preferably a compound represented by the following formula (1-1), and more preferably a compound represented by the formula (1-1) wherein $R^2$ is a methylene group.

[Chem. 8]

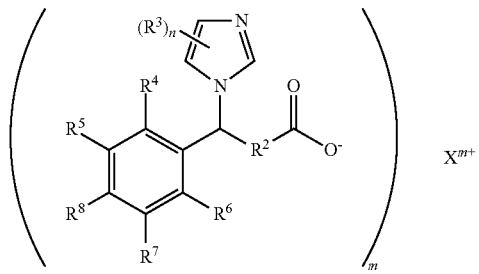

(1-1)

(In the formula (1-1), X, $R^2$, $R^3$, m and n are the same as those defined in the formula (1); and $R^4$, $R^5$, $R^6$, $R^7$, and $R^8$ are each independently a hydrogen atom, a halogen atom, a hydroxyl group, a mercapto group, a sulfide group, a silyl group, a silanol group, a nitro group, a nitroso group, a sulfino group, a sulfo group, a sulfonate group, a phosphino group, a phosphinyl group, a phosphono group, a phosphonate group, an amino group, an ammonio group, or an organic group, wherein at least one of $R^4$, $R^5$, $R^6$, $R^7$, and $R^8$ is a group other than a hydrogen atom. At least two of $R^4$, $R^5$, $R^6$, $R^7$, and $R^8$ may be bonded to each other to form a cyclic structure. $R^2$ and $R^6$ may be bonded to each other to form a cyclic structure.)

When $R^4$, $R^5$, $R^6$, $R^7$, and $R^8$ are organic groups, the organic groups are the same as an organic group, which $R^8$ in the formula (1) has as a substituent. $R^4$, $R^5$, $R^6$, and $R^7$ are preferably a hydrogen atom in view of solubility of the above compound in solvent.

Among these, at least one of $R^4$, $R^5$, $R^6$, $R^7$, and $R^8$ is preferably the following substituent. Particularly preferably, $R^8$ is the following substituent. When $R^8$ is the following substituent, $R^4$, $R^5$, $R^6$, and $R^7$ are preferably a hydrogen atom.

—O—$R^9$ ($R^9$ is a hydrogen atom or an organic group.)

When $R^9$ is an organic group, the organic group is the same as an organic group, which $R^1$ in the formula (1) has as a substituent. $R^9$ is preferably an alkyl group, more preferably, an alkyl group having 1 or more and 8 or less carbon atoms, particularly preferably an alkyl group having 1 or more and 3 or less carbon atoms, and most preferably a methyl group.

Among the compounds represented by the formula (1-1) mentioned above, a compound represented by the following formula (1-1-1) is preferable.

[Chem. 9]

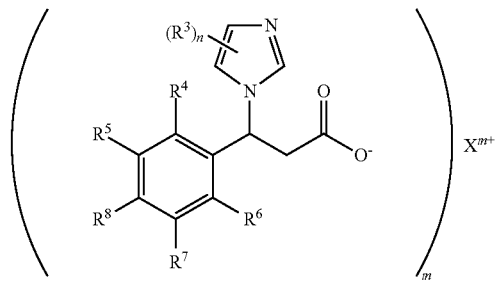

(1-1-1)

(In the formula (1-1-1), X, $R^3$, $R^4$, $R^5$, $R^6$, $R^7$, and $R^8$, m and n are the same as those in the formula (1) except that at least one of $R^4$, $R^5$, $R^6$, $R^7$, and $R^8$ is a group other than a hydrogen atom.)

Among the compounds represented by the formula (1-1-1), at least one of $R^4$, $R^5$, $R^6$, $R^7$, and $R^8$ is preferably represented by the above-mentioned —O—$R^9$; and $R^8$ is particularly preferably a group represented by —O— $R^9$. When $R^8$ is a group represented by —O— $R^9$, $R^4$, $R^5$, $R^6$, and $R^7$ are preferably hydrogen atoms.

Suitable specific examples of the compound represented by the formula (1) include the following.

[Chem. 10]

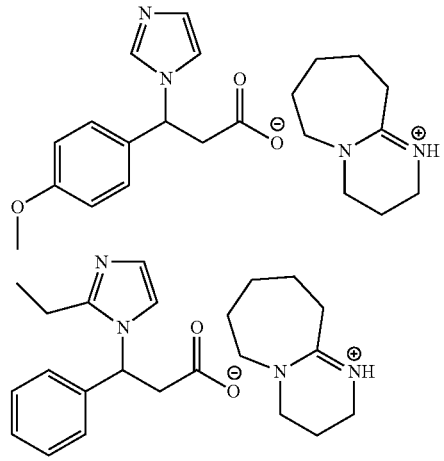

15
-continued
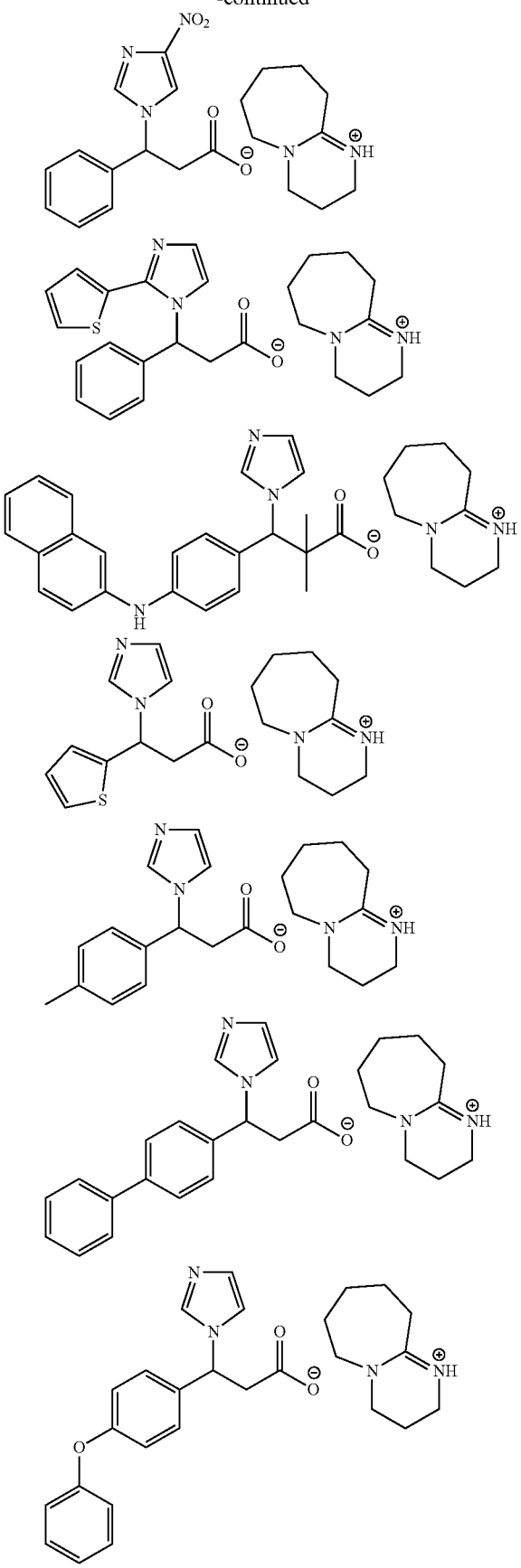
16
-continued
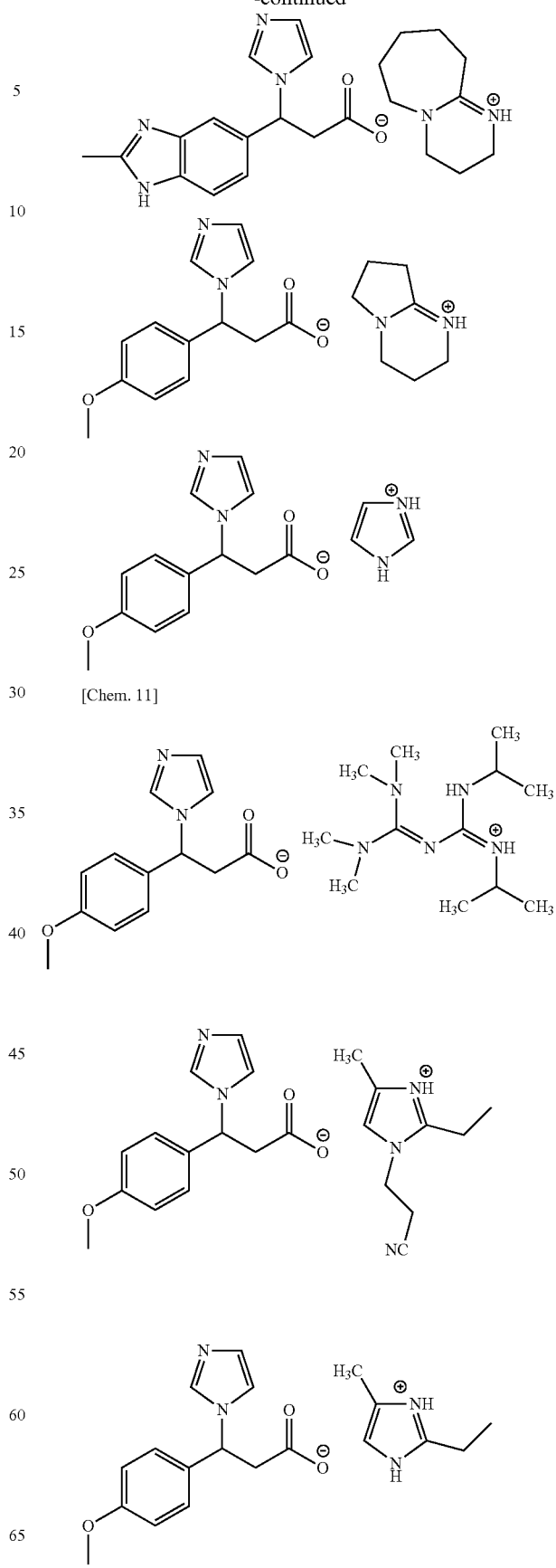
[Chem. 11]

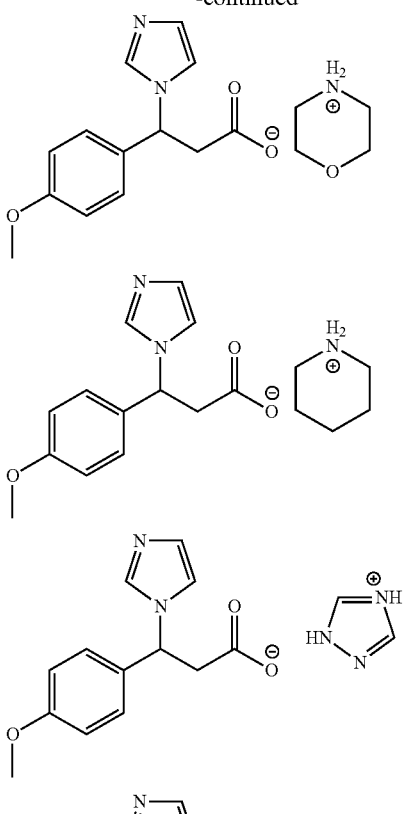
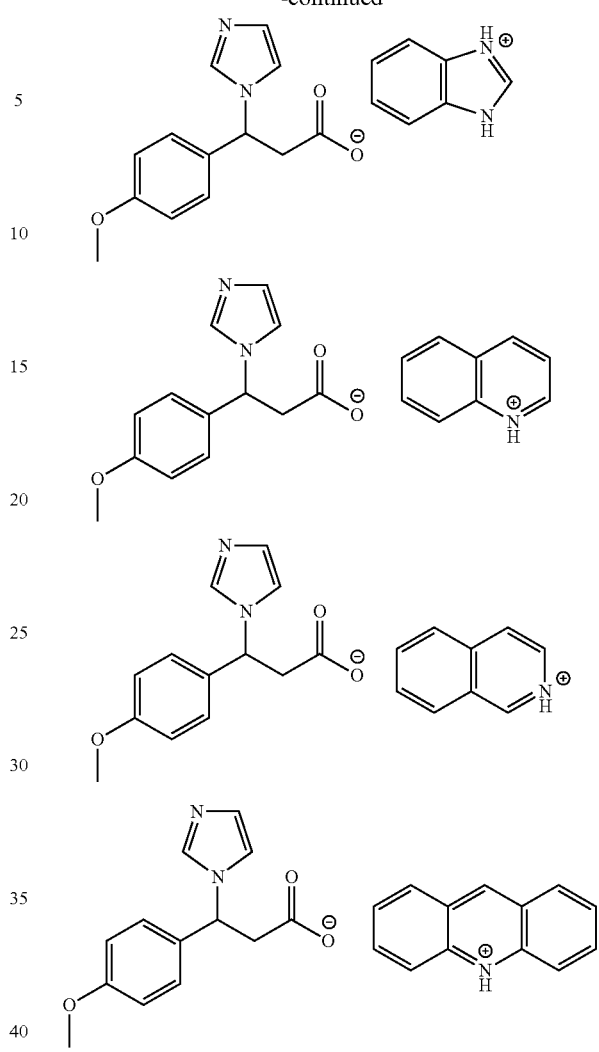

-continued

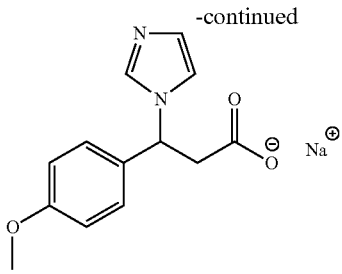

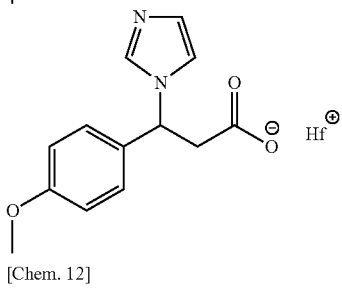

[Chem. 12]

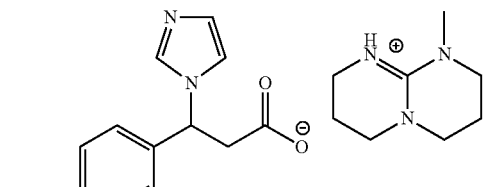

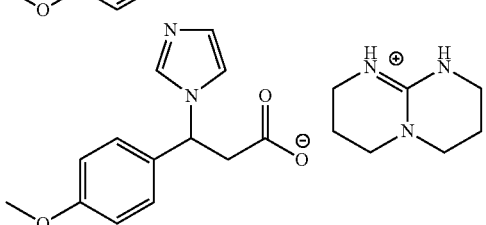

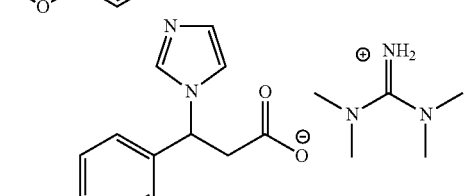

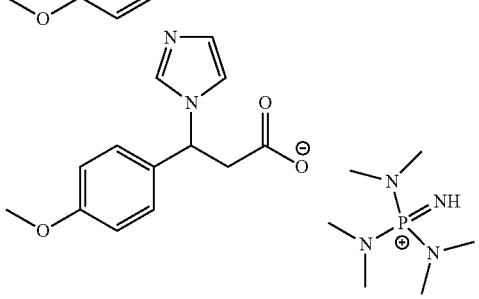

<<Applications of Use>>

The compound represented by the above formula (1) according to the first aspect can be used as an epoxy curing catalyst. The epoxy curing catalyst according to the second aspect includes the compound represented by the above formula (1) according to the first aspect. It is preferable that the compound represented by the above formula (1) and the epoxy compound are mixed by, for example, a stirrer to prepare a curable composition. Temperature and time for curing the above-mentioned curable composition are not particularly limited as long as curing sufficiently progresses. For example, a curable composition is cured at about 100° C. or more and 200° C. or less for 3 minutes or more and 10 minutes or less. The above-mentioned curable composition can be cured at a low temperature, but it may also be cured at a high temperature. The content of the compound represented by the above formula (1) in the above-mentioned composition is not particularly limited. The content of the compound represented by the above formula (1) in the above-mentioned composition is, for example, preferably 0.01% by mass or more and 80% by mass or less, more preferably 0.1% by mass or more and 40% by mass or less, further preferably 0.5% by mass or more and 30% by mass or less, and particularly preferably 1% by mass or more and 15% by mass or less with respect to the entire composition (excluding a solvent). The above-mentioned composition may contain various additives as necessary. Examples of the additives include a coloring agent, a dispersing agent, a sensitizer, a curing accelerator, a filler, an adhesion promoter, an antioxidant, an ultraviolet absorber, an aggregation inhibitor, a thermal polymerization inhibitor, an antifoaming agent, a surfactant, and the like.

The epoxy compound cured by the compound of the first aspect is not particularly limited as long as it is a compound including an epoxy group. The epoxy compound can be selected from various compounds having an epoxy group conventionally blended in the curable composition. The epoxy compound may be a non-polymer low-molecular weight compound having an epoxy group or a polymer having an epoxy group. Hereinafter, with respect to the epoxy compound, a non-polymer having an epoxy group and a polymer having an epoxy group are described sequentially.

(Non-Polymer Having an Epoxy Group)

A non-polymer having an epoxy group can be appropriately selected from various non-polymer type epoxy compounds which have conventionally been blended in a curable composition. Suitable examples of the epoxy compound include difunctional epoxy resin such as bisphenol A type epoxy resin, bisphenol F type epoxy resin, bisphenol S type epoxy resin, bisphenol AD type epoxy resin, naphthalene type epoxy resin, and biphenyl type epoxy resin; glycidyl ester type epoxy resin such as dimer acid glycidyl ester and triglycidyl ester; glycidyl amine type epoxy resin such as tetraglycidyl aminodiphenylmethane, triglycidyl-p-aminophenol, tetraglycidyl metaxylylenediamine, and tetraglycidyl bisaminomethylcyclohexane; heterocyclic epoxy resin such as triglycidyl isocyanurate; trifunctional epoxy resin such as phloroglucinol triglycidylether, trihydroxybiphenyl triglycidylether, trihydroxyphenylmethane triglycidylether, glycerin triglycidylether, 2-[4-(2,3-epoxypropoxy)phenyl-2-[4-[1,1-bis[4-(2,3-epoxypropxy)phenyl]ethyl]phenyl]propane, and 1,3-bis[4-[1-[4-(2,3-epoxypropoxy)phenyl]-1-[4-[1-[4-(2,3-epoxypropoxy)phenyl]-1-methylethyl]phenyl] ethyl]phenoxy]-2-propanol; and tetrafunctional epoxy resin such as tetrahydroxyphenylethane tetraglycidylether, tetraglycidyl benzophenone, bisresorcinol tetraglycidylether, and tetraglycidoxybiphenyl.

From the viewpoint that a cured product formed using a curable composition is excellent in its mechanical property, an aliphatic epoxy compound that does not include an aromatic group is also preferable. Among the aliphatic epoxy compounds, from the viewpoint of providing a cured product having excellent transparency and hardness, an aliphatic epoxy compound having an alicyclic epoxy group is preferable. Specific examples of the aliphatic epoxy compound having an alicyclic epoxy group include 2-(3,4- epoxycyclohexyl-5,5-spiro-3,4-epoxy)cyclohexane-metadioxane, bis(3,4-epoxycyclohexylmethyl)adipate, bis(3,4-epoxy-6-methylcyclohexylmethyl)adipate, 3,4-epoxy-6-methylcyclohexyl-3',4'-epoxy-6'-methylcyclohexane carboxylate, ε-caprolactone-modified 3,4-epoxycyclohexylmethyl-3',4'-epoxycyclohexane carboxylate, trimethylcaprolactone-modified 3,4-epoxycyclohexylmethyl-3',4'-epoxycyclohexane carboxylate, β-methyl-δ-valerolactone-modified 3,4-epoxycyclohexylmethyl-3',4'-epoxycyclohexane carboxylate, methylenebis(3,4-epoxycyclohexane), di(3,4-epoxycyclohexylmethyl)ether of ethylene glycol, ethylenebis(3,4-epoxycyclohexane carboxylate), dioctyl epoxycyclohexahydrophthalate, di-2-ethylhexyl epoxycyclohexahydrophthalate, an epoxy resin having a tricyclodecene oxide group, and the like.

(Polymer Having an Epoxy Group)

A polymer having an epoxy group may be a polymer obtained by polymerizing a monomer having an epoxy group or a monomer mixture including a monomer having an epoxy group or a polymer in which an epoxy group is introduced into a polymer having a functional group having reactivity, for example, a hydroxyl group, a carboxy group, an amino group, and the like, using a compound having an epoxy group, for example, epichlorohydrin. Furthermore, partial oxide of a polymer having an unsaturated aliphatic hydrocarbon group in the side chain, for example, 1,2-polybutadiene, can be suitably used as a polymer having an epoxy group. Such partial oxide includes an epoxy group generated by oxidizing an unsaturated bond included in the side chain.

Because of ease of availability, preparation and adjustment of an amount of an epoxy group in the polymer, as the polymer having an epoxy group, a polymer obtained by polymerizing a monomer having an epoxy group or a monomer mixture including a monomer having an epoxy group, and a partial a polymer having an unsaturated aliphatic hydrocarbon group in the side chain are preferable.

(Monomer Having Epoxy Group or Monomer Mixture Including Monomer Having Epoxy Group)

Among the polymers having an epoxy group, because of ease of preparation, or coating characteristics of a curable composition to a base material, or the like, a homopolymer of a (meth)acrylic acid ester having an epoxy group, or a copolymer of a (meth)acrylic acid ester having an epoxy group and other monomers is preferable.

The (meth)acrylic acid ester having an epoxy group may be either a chain aliphatic (meth)acrylic acid ester having an epoxy group, or the below-mentioned (meth)acrylic acid ester having an alicyclic epoxy group. Furthermore, the (meth)acrylic acid ester having an epoxy group may have an aromatic group. From the viewpoint of transparency of a cured product formed using a curable composition, the (meth)acrylic acid ester having an epoxy group is preferably an aliphatic (meth)acrylic acid ester having a chain aliphatic epoxy group or an aliphatic (meth)acrylic acid ester having an alicyclic epoxy group, and more preferably an aliphatic (meth)acrylic acid ester having an alicyclic epoxy group.

Examples of the (meth)acrylic acid ester, which has an aromatic group and an epoxy group, include 4-glycidyloxyphenyl (meth)acrylate, 3-glycidyloxyphenyl (meth)acrylate, 2-glycidyloxyphenyl (meth)acrylate, 4-glycidyloxyphenylmethyl (meth)acrylate, 3-glycidyloxyphenylmethyl (meth)acrylate, and 2-glycidyloxyphenylmethyl (meth)acrylate.

Examples of the aliphatic (meth)acrylic acid ester having a chain aliphatic epoxy group include (meth)acrylic acid esters in which a chain aliphatic epoxy group is combined with an oxy group (—O—) in an ester group (—O—CO—), such as epoxyalkyl (meth)acrylate and epoxyalkyloxyalkyl (meth)acrylate. Such a chain aliphatic epoxy group possessed by the (meth)acrylic acid ester may have one or plural oxy group(s) (—O—) in a chain. The number of carbon atoms of the chain aliphatic epoxy group is not particularly limited, and is preferably 3 or more and 20 or less, more preferably 3 or more and 15 or less, and particularly preferably 3 or more and 10 or less.

Specific examples of the aliphatic (meth)acrylic acid ester having a chain aliphatic epoxy group include epoxyalkyl (meth)acrylates such as glycidyl (meth)acrylate, 2-methyl glycidyl (meth)acrylate, 3,4-epoxybutyl (meth)acrylate, and 6,7-epoxyheptyl (meth)acrylate; and epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-hexyl (meth)acrylate, and 6-glycidyloxy-n-hexyl (meth)acrylate. The cured product obtained by curing the above-mentioned curable composition can be used as protective films for electronic components, such as a liquid crystal display element, an integrated circuit element, a solid-state image sensing device, and the like, an interlayer insulating film, a flat film, and an insulating film. When the cured product is a film, the thickness is preferably 10 nm or more and 100 μm or less, more preferably 50 nm or more and 10 μm or less, and further preferably 100 nm or more and 5000 nm or less.

<<Method for Producing a Compound Represented by the Above Formula (1)>>

A third aspect is a method for producing a compound represented by the above formula (1) of the first aspect, the method including producing the compound represented by the above formula (1) by neutralizing the compound represented by the formula (10) and a base capable of forming an m-valent counter cation $X^{m+}$ in the presence or absence of a solvent.

[Chem. 13]

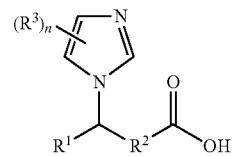

(10)

(In the formula (10), $R^1$, $R^2$, $R^3$, and n are the same as those in the formula (1), and specific examples and preferable examples thereof are the same.) The base capable of forming an m-valent counter cation $X^{m+}$ is preferably an acyclic or cyclic nitrogen-containing aliphatic compound, a nitrogen-containing aromatic compound, or a metal atom or an atomic group including the metal atom. It is preferable that the base capable of forming an m-valent counter cation $X^{m+}$ is a base capable of forming an acyclic or cyclic nitrogen-containing aliphatic cation represented by any one of the above formulae (2) to (4), a nitrogen-containing aromatic cation represented by any one of the above formulae (5) to (13), a nitrogen-containing aliphatic cation represented by any one of the above formulae (14) to (16), or a cation of atomic group including a metal element selected from the group consisting of a typical metal element, a transition metal element and a semimetal element.

Examples of the method for neutralizing the compound represented by the above formula (10) and the above base in a solvent include a method of mixing the compound represented by the above formula (10) and the above base in, for example, a polar solvent, under heating or without heating. Examples of the above polar solvent include alcohol, and specific examples include methanol, ethanol, propanol, isopropanol, butanol, tert-butanol, and the like. Under heating, the compound represented by the above formula (10) and the above base can be dissolved in the above solvent and mixed. Heating temperature is, for example, 40° C. or more, preferably 50° C. or more, and more preferably 55° C. or more. The upper limit of the temperature at the time of heating is not particularly limited, but, preferably, it is a temperature of a boiling point or less of the above solvent. Without heating, the compound represented by the above formula (10) or the above base may not be easily dissolved in a solvent. In this case, as a salt formation proceeds, an amount of insoluble matter in the reaction solution can be reduced.

A method for neutralizing a compound represented by the above formula (10) and the above base in the absence of a solvent is not particularly limited as long as the method is capable of bringing the compound represented by the above formula (10) and the above base into contact with each other. Specific examples of methods include a method of mixing while pulverizing or grinding down the solid compound represented by the above formula (10) and the solid or liquid base mentioned above in a mortar and the like at an ordinary temperature.

Furthermore, the ratio (molar ratio) of the compound represented by the above formula (10) and the above base is not particularly limited, but a value of M1/(M2/m) is preferably 20/80 to 80/20, and more preferably 30/70 to 70/30 where M1 denotes the number of moles of the compound represented by the formula (10) and M2 denotes the number of moles of the above base giving the m-valent counter cation $X^{m+}$.

Furthermore, when a compound represented by the above formula (1) wherein $X^{m+}$ is a sodium cation and a potassium cation, and a base capable of forming an m-valent counter cation $X^{m+}$ other than the sodium cation and the potassium are mixed with each other to carry out salt replacement, it is possible to manufacture a compound represented by the above formula (1) in which $X^{m+}$ is cations other than a sodium cation and a potassium cation.

EXAMPLES

Hereinafter, the present invention will be described more detail based on the Examples. The present invention is not limited to these Examples.

[Synthesis Example 1] Synthesis 1 of a Compound Represented by the Above Formula (1)

[Chem. 14]

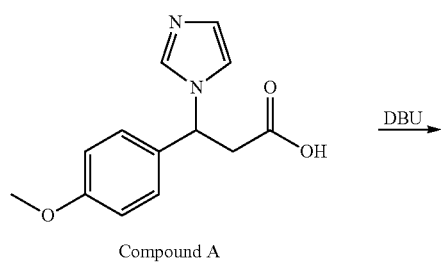

Compound A

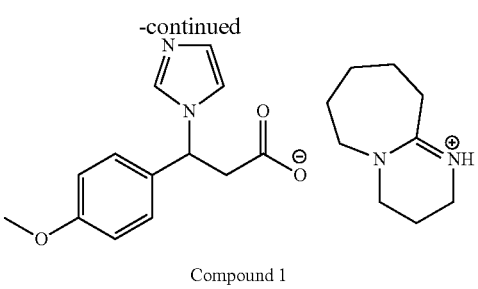

Compound 1

Compound A (2.00 g, 8.12 mmol) and methanol (20 g) were added into a 50 ml three-necked flask. The inside of the flask was subjected to replacement by nitrogen, followed by heating in a water bath at 60° C. to dissolve the compound A. Next, diazabicycloundecene (DBU; 1.24 g, 8.12 mmol) was dropped, and reacted at 60° C. for four hours according to the above scheme. After completion of the reaction, the reacted product was cooled to room temperature (25° C.). Then, the solvent was removed by evaporation from the reaction solution using a rotary evaporator to obtain a compound represented by the above formula (1) (compound 1). (produced amount=3.27 g, yield=95%, yellow viscous liquid)

$^1$H-NMR (heavy DMSO, 400 MHz): cation δ (ppm)=3.48 (CH$_2$, 2H), 3.40 (CH$_2$, 2H), 3.15 (CH$_2$, 2H), 2.65 (CH$_2$, 2H), 1.82 (CH$_2$, 2H), 1.70-1.45 (CH$_2$, 6H), Anion δ (ppm)=7.70 (CH, 1H), 7.22 (Ph, 2H), 7.15 (CH, 1H), 6.85 (Ph, 2H), 6.80 (CH, 1H), 5.63 (CH, 1H), 3.70 (CH$_3$, 3H), 2.85-2.65 (CH$_2$, 2H)

[Synthesis Example 2] Synthesis 2 of a Compound Represented by the Above Formula (1)

[Chem. 15]

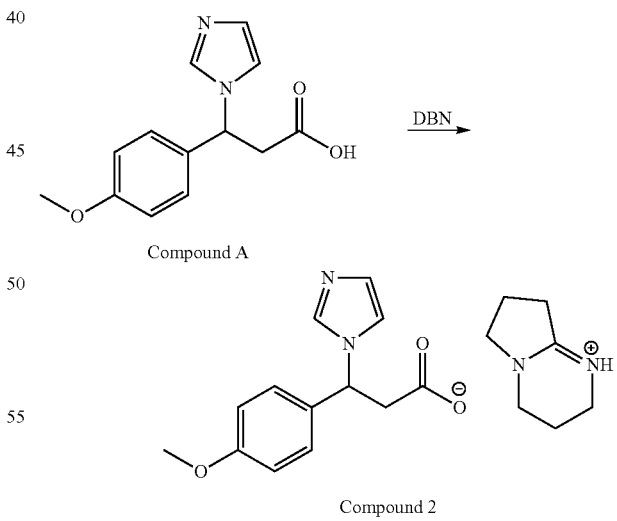

Compound 2

Compound A (2.00 g, 8.12 mmol) and methanol (20 g) were added into a 50 ml three-necked flask. The inside of the flask was subjected to replacement by nitrogen, followed by heating in a water bath at 60° C. to dissolve the compound A. Next, diazabicyclononene (DBN; 1.11 g, 8.12 mmol) was dropped, and the compound A and DBN were reacted with each other at 60° C. for four hours according to the above scheme. After completion of the reaction, the reaction solution was cooled to room temperature. Then, the solvent was removed by evaporation from the reaction solution using a rotary evaporator to obtain a compound represented by the above formula (1) (compound 2). (produced amount=2.91 g, yield=90%, yellow viscous liquid)

$^1$H-NMR (heavy DMSO, 400 MHz): cation δ (ppm)=3.55 ($CH_2$, 2H), 3.40-3.25 ($CH_2$, 4H), 2.81 ($CH_2$, 2H), 2.00 ($CH_2$, 2H), 1.88 ($CH_2$, 2H)

Anion δ (ppm)=7.70 (CH, 1H), 7.22 (Ph, 2H), 7.15 (CH, 1H), 6.85 (Ph, 2H), 6.80 (CH, 1H), 5.63 (CH, 1H), 3.70 ($CH_3$, 3H), 2.85-2.65 ($CH_2$, 2H)

[Synthesis Example 3] Synthesis 3 of a Compound Represented by the Above Formula (1)

[Chem. 16]

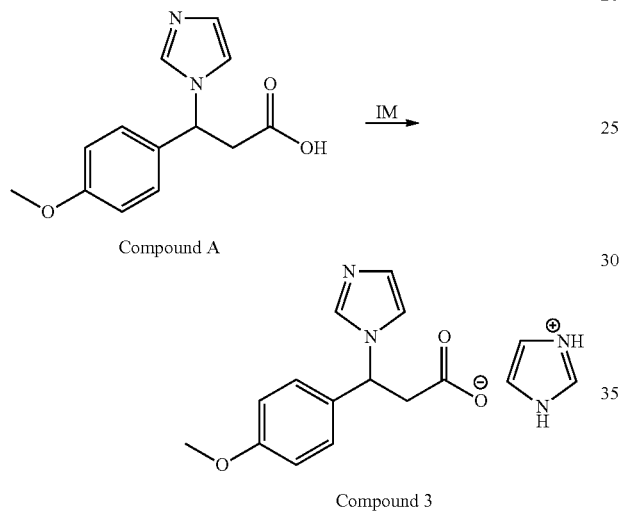

Compound A (2.00 g, 8.12 mmol) and methanol (20 g) were added into a 50 ml three-necked flask. The inside of the flask was subjected to replacement by nitrogen, followed by heating in a water bath at 60° C. to dissolve the compound A. Next, imidazole (IM; 0.55 g, 8.12 mmol) was added, and the compound A and IM were reacted with each other at 60° C. for four hours. After completion of the reaction, the reaction solution was cooled to room temperature. Then, the solvent was removed by evaporation from the reaction solution using a rotary evaporator to obtain a compound represented by the above formula (1) (compound 3). (produced amount=2.43 g, yield=95%, white solid)

$^1$H-NMR (heavy DMSO, 400 MHz): cation δ (ppm)=7.03 (CH, 2H), 7.65 (CH, 1H)

Anion δ (ppm)=7.86 (CH, 1H), 7.35 (3H), 6.99 (3H), 5.70 (CH, 1H), 3.71 ($CH_3$, 3H), 3.35-3.16 ($CH_2$, 2H)

Compound A simple substance and an imidazole simple substance as raw materials, and the obtained compound 3 were subjected to measurement of X-ray diffraction patterns using an X-ray diffraction measuring device (manufactured by Rigaku Corporation; product name "Fully automatic horizontal multi-objective X-ray diffractometer SmartLab") in the following conditions. Since the obtained compound 3 showed a reflection pattern different from both of the raw material simple substances, it was decided that the compound 3 be not a mere mixture but a salt.

X-ray used: CuKα ray derived from rotating anticathode-type X-ray generator, 45 kV-200 mA Scanning rate (2θ): 4.0°/min Divergence slit: (⅔°)

Scattering slit: (⅔°)

Other conditions are standard conditions settings for package measurements "Generic Measurement>Generic (concentration method)"

[Synthesis Example 4] Synthesis 4 of a Compound Represented by the Above Formula (1)

[Chem. 17]

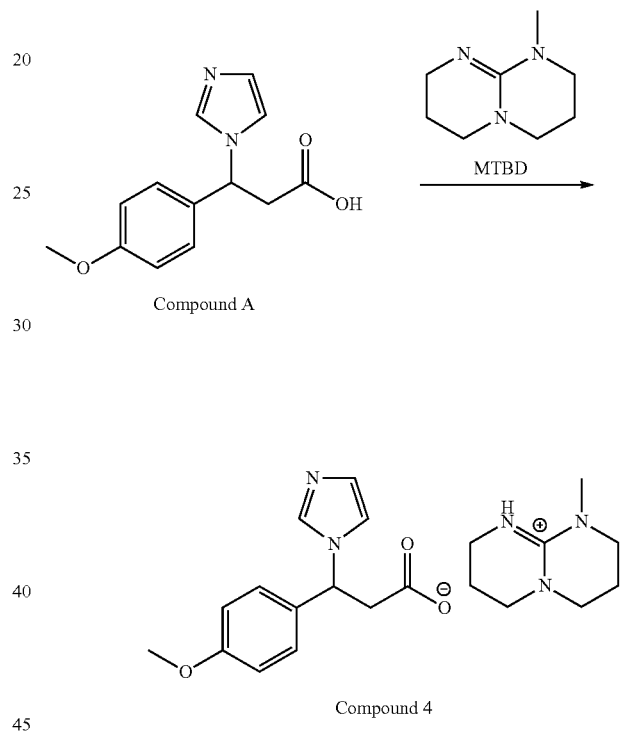

Compound A (1.60 g, 6.50 mmol) and tetrahydrofuran (3 g) were added into a 20 ml eggplant flask. The inside of the eggplant flask was subjected to replacement by nitrogen, followed by heating in an oil bath at 60° C. to dissolve the compound A in tetrahydrofuran. Next, 7-methyl-1,5,7-triazabicyclo[4.4.0]dec-5-ene (MTBD; 1.00 g, 6.50 mmol) was dropped, and compound A and MTBD were reacted at 60° C. for 30 minutes according to the above scheme. After completion of the reaction, the reaction solution was cooled to room temperature. Then, the solvent was removed by evaporation from the reaction solution using a rotary evaporator to obtain a compound represented by the above formula (1) (compound 4). (produced amount=2.5 g, yield=95%, yellow viscous liquid)

$^1$H-NMR (heavy DMSO, 500 MHz): cation δ (ppm)=9.20 (NH, 1H), 3.27-3.22 (6H), 3.17-3.15 (2H), 2.90 ($CH_3$, 3H), 1.92-1.89 (2H), 1.81-1.79 (2H)

Anion δ (ppm)=7.67 (CH, 1H), 7.21 (2H), 7.12 (1H), 6.84 (2H), 6.79 (1H), 5.62 (CH, 1H), 3.71 ($CH_3$, 3H), 2.73-2.61 ($CH_2$, 2H)

[Synthesis Example 5] Synthesis 5 of a Compound Represented by the Above Formula (1)

[Chem. 18]

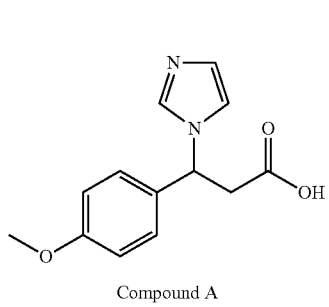 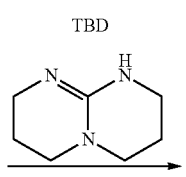

Compound A          TBD

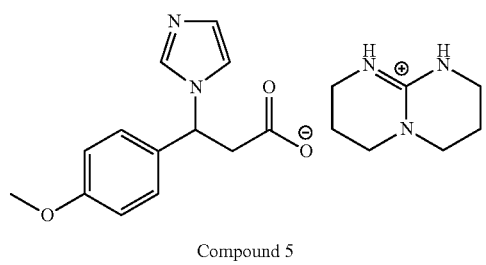

Compound 5

Compound A (1.50 g, 6.09 mmol) and methanol (9 g) were added into a 20 ml eggplant flask. The eggplant flask was subjected to replacement by nitrogen, followed by heating in an oil bath at 60° C. to dissolve the compound A in methanol. Next, 1,5,7-triazabicyclo[4,4,0]dac-5-ene (TBD; 0.85 g, 6.09 mmol) was dropped, and the compound A and TBD were reacted at 60° C. for 30 minutes according to the above scheme. After completion of the reaction, the reaction solution was cooled to room temperature. Then, the solvent was removed by evaporation from the reaction solution using a rotary evaporator to obtain a compound represented by the above formula (1) (compound 5). (produced amount=2.2 g, yield=95%, yellow solid)

$^1$H-NMR (heavy DMSO, 500 MHz): cation δ (ppm)=10.48 (NH, 2H), 3.22-3.17 (4H), 3.10-3.07 (4H), 1.86-1.81 (4H)

Anion δ (ppm)=7.71 (CH, 1H), 7.25 (2H), 7.17 (1H), 6.86 (2H), 6.80 (1H), 5.65 (CH, 1H), 3.71 (CH$_3$, 3H), 2.87-2.73 (CH$_2$, 2H)

[Synthesis Example 6] Synthesis 6 of a Compound Represented by the Above Formula (1)

[Chem. 19]

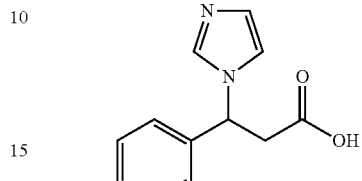 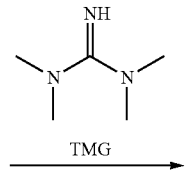

Compound A          TMG

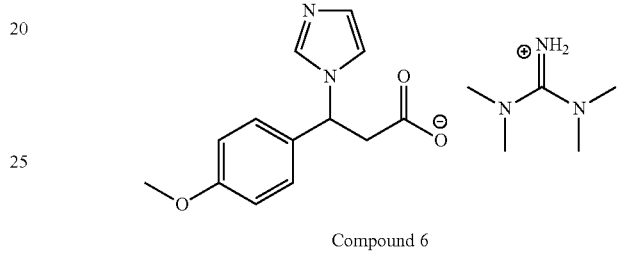

Compound 6

Compound A (1.50 g, 6.09 mmol) and methanol (9 g) were added into a 20 ml eggplant flask. The inside of the eggplant flask was subjected to replacement by nitrogen, followed by heating by an oil bath at 60° C. to dissolve the compound A in methanol. Next, 1,1,3,3-tetramethylguanidine (TMG; 0.7 g, 6.09 mmol) was dropped, and the compound A and TMG were reacted with each other at 60° C. for 30 minutes according to the above scheme. After completion of the reaction, the reaction solution was cooled to room temperature. Then, the solvent was removed by evaporation from the reaction solution using a rotary evaporator to obtain a compound represented by the above formula (1) (compound 6). (produced amount=2.2 g, yield=100%, yellow solid)

$^1$H-NMR (heavy DMSO, 500 MHz): cation δ (ppm)=2.84 (6H) Anion δ (ppm)=7.67 (CH, 1H), 7.21 (2H), 7.12 (1H), 6.85 (2H), 6.79 (1H), 5.62 (CH, 1H), 3.71 (CH$_3$, 3H), 2.28-2.64 (CH$_2$, 2H)

[Synthesis Example 7] Synthesis 7 of a Compound Represented by the Above Formula (1)

[Chem. 20]

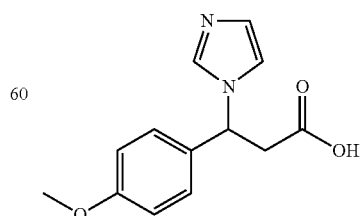 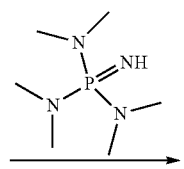

Compound A

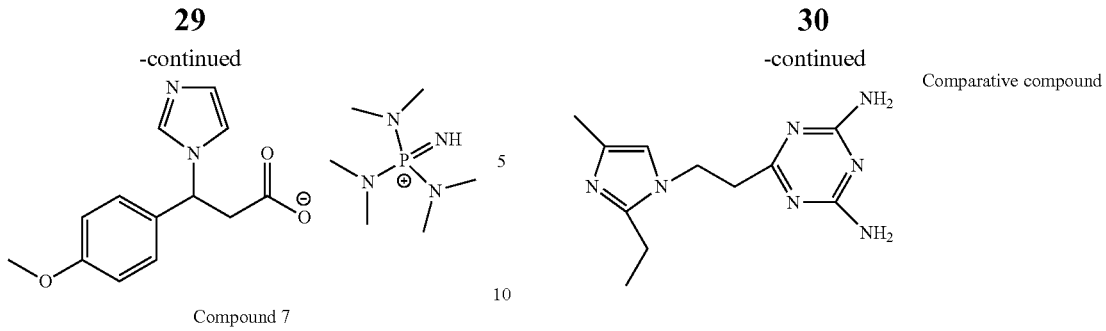

Compound 7

Compound A (1.00 g, 4.06 mmol) and methanol (9 g) were added into a 20 ml eggplant flask. The inside of the eggplant flask was subjected to replacement by nitrogen, followed by heating in an oil bath at 60° C. to dissolve the compound A in methanol. Next, imino-tris(dimethylamino) phosphorane (0.72 g, 4.06 mmol) was dropped and the compound A and imino-tris(dimethylamino)phosphorane were reacted at 60° C. for 30 minutes according to the above scheme. After completion of the reaction, the reaction solution was cooled to room temperature. Then, the solvent was removed by evaporation from the reaction solution using a rotary evaporator to obtain a compound represented by the above formula (1) (compound 7). (produced amount=1.7 g, yield=98%, yellow solid)

$^1$H-NMR (heavy DMSO, 500 MHz): cation δ (ppm)=2.63 (9H), 2.61, 9H), anion δ (ppm)=7.65 (CH, 1H), 7.18 (2H), 7.10 (1H), 6.84 (2H), 6.84 (1H), 5.61 (CH, 1H), 3.71 (CH$_3$, 3H), 2.28-2.64 (CH$_2$, 2H)

[Preparation of Composition]

The following epoxy compound, the compound represented by the formula (1), and the comparative compound were mixed in the blending ratio (parts by mass) shown in the following Table 1 to prepare the compositions of Example 1 and Comparative Example 1.

TABLE 1

|  | Epoxy compound (part by mass) | Compound (part by mass) |
|---|---|---|
| Example 1 | The following epoxy compound (95) | Compound 3 (5) |
| Comparative Example 1 | The following epoxy compound (95) | Comparative compound (5) |

[Chem. 21]

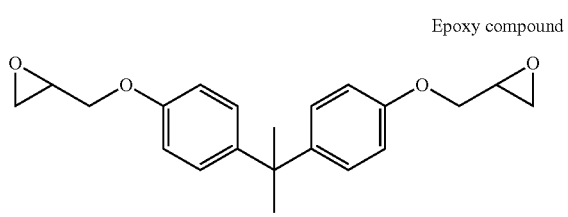

Epoxy compound

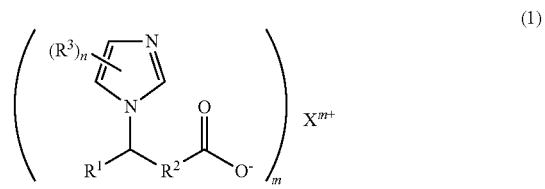

Comparative compound

[Heat Resistance Evaluation]

The compositions of Example 1 and Comparative Example 1 were evaluated for heat resistance. The compositions of Example 1 and Comparative Example 1 were applied to a glass substrate and heated at 200° C. (five minutes) to obtain a cured film having a film thickness of 1 μm. The obtained cured film was cooled to room temperature once, and the temperature was increased from room temperature to 200° C. again, and the state of the film was verified. The cured film of Comparative Example 1 started to melt around 140° C., but the cured film of Example 1 did not melt. Also, the endothermic peak did not appear in observation using a differential scanning calorimeter (product name: DSC-50, manufactured by Shimadzu Corporation). Therefore, it is considered that a cured film having excellent heat resistance has been obtained.

The invention claimed is:

1. A compound represented by the following formula (1):

$$(1)$$

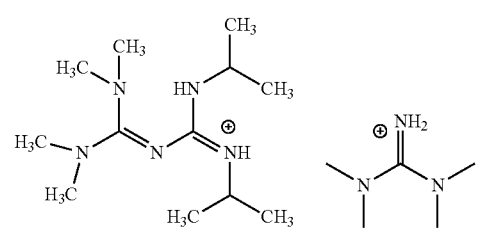

wherein $X^{m+}$ represents an m-valent counter cation; $R^1$ represents an optionally substituted aromatic group; $R^2$ represents an optionally substituted alkylene group; $R^3$ represents a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; m is an integer of 1 or more; n is an integer of 0 or more and 3 or less; and $R^2$ may be bonded to $R^1$ to form a cyclic structure wherein the m-valent counter cation $X^{m+}$ is acyclic or cyclic nitrogen-containing aliphatic cation, or a nitrogen-containing aromatic cation, and wherein the acyclic nitrogen-containing aliphatic cation is selected from the group consisting of the following three cations:

-continued

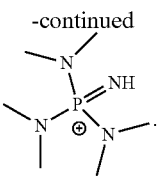

2. A method of using the compound according to claim 1 as an epoxy curing catalyst, the method comprising curing an epoxy compound in the presence of the compound according to claim 1.

3. A method for producing the compound according to claim 1, the method comprising: producing the compound represented by the formula (1) by neutralizing the compound represented by the formula (10) and a base capable of forming an m-valent counter cation $X^{m+}$ in presence or absence of a solvent,

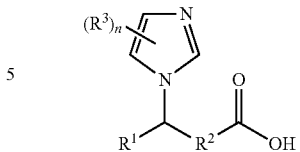

(10)

wherein, in the formula (10), $R^1$ is an optionally substituted aromatic group; $R^2$ is an optionally substituted alkylene group; $R^3$ is a halogen atom, a hydroxyl group, a mercapto group, a sulfide group, a silyl group, a silanol group, a nitro group, a nitroso group, a sulfonate group, a phosphino group, a phosphinyl group, a phosphonate group, or an organic group; n is an integer of 0 or more and 3 or less; and $R^2$ may be bonded to $R^1$ to form a cyclic structure.

4. The method according to claim 3, wherein the base capable of forming the m-valent counter cation $X^{m+}$ is an acyclic or cyclic nitrogen-containing aliphatic compound, or a nitrogen-containing aromatic compound.

\* \* \* \* \*